US009462811B2

(12) United States Patent
Martin et al.

(10) Patent No.: US 9,462,811 B2
(45) Date of Patent: *Oct. 11, 2016

(54) METHODS FOR IMPROVING PLANT GROWTH

(71) Applicant: FMC Corporation, Philadelphia, PA (US)

(72) Inventors: Timothy M. Martin, Ringoes, NJ (US); Frank Zawacki, Yardley, PA (US)

(73) Assignee: FMC Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/640,285

(22) Filed: Mar. 6, 2015

(65) Prior Publication Data
US 2015/0264937 A1 Sep. 24, 2015

Related U.S. Application Data

(63) Continuation of application No. 14/217,603, filed on Mar. 18, 2014, now Pat. No. 8,993,484.

(51) Int. Cl.
*A01N 59/06* (2006.01)
*A01N 25/30* (2006.01)

(52) U.S. Cl.
CPC .................... *A01N 59/06* (2013.01)

(58) Field of Classification Search
CPC ............... A01N 59/06; A01N 25/30
See application file for complete search history.

(56) References Cited

U.S. PATENT DOCUMENTS

| | | | |
|---|---|---|---|
| 3,060,084 A | 10/1962 | Littler | |
| 4,360,376 A | 11/1982 | Koestler | |
| 5,583,090 A | 12/1996 | Stern et al. | |
| 5,834,006 A | 11/1998 | Smith et al. | |
| 5,925,464 A | 7/1999 | Mulqueen et al. | |
| 7,094,592 B2 | 8/2006 | Watanabe et al. | |
| 8,029,827 B2 | 10/2011 | Martin | |
| 8,263,527 B2 | 9/2012 | Martin | |
| 8,293,733 B2 | 10/2012 | Casana Giner et al. | |
| 8,524,222 B2 | 9/2013 | Jacobsen et al. | |
| 8,937,054 B1 | 1/2015 | Martin | |
| 8,993,484 B1 * | 3/2015 | Martin ................ | A01N 59/06 424/683 |
| 2002/0115565 A1 | 8/2002 | Asrar et al. | |
| 2004/0023802 A1 | 2/2004 | Asrar et al. | |
| 2006/0166898 A1 | 7/2006 | Chen | |
| 2007/0135506 A1 | 6/2007 | Zeun et al. | |
| 2008/0206361 A1 | 8/2008 | Martin | |
| 2008/0306026 A1 | 12/2008 | Shirley | |
| 2009/0203746 A1 | 8/2009 | Jadhav et al. | |
| 2010/0016392 A1 | 1/2010 | Kabanov et al. | |
| 2010/0179198 A1 | 7/2010 | Mertoglu et al. | |
| 2010/0234225 A1 | 9/2010 | Dexter et al. | |
| 2011/0033436 A1 | 2/2011 | Chen et al. | |
| 2011/0053776 A1 | 3/2011 | Bahr | |
| 2012/0009238 A1 | 1/2012 | Brahm | |
| 2012/0184589 A1 | 7/2012 | Gewehr et al. | |
| 2013/0123104 A1 | 5/2013 | McKnight et al. | |
| 2013/0236522 A1 | 9/2013 | Misumi | |
| 2014/0342914 A1 | 11/2014 | Joost et al. | |
| 2015/0099626 A1* | 4/2015 | Martin ................ | A01N 43/16 504/101 |
| 2015/0099627 A1* | 4/2015 | Martin ................ | A01N 57/16 504/101 |
| 2015/0099628 A1* | 4/2015 | Martin ................ | A01N 53/00 504/101 |

FOREIGN PATENT DOCUMENTS

| | | |
|---|---|---|
| EP | 2716748 A1 | 4/2014 |
| WO | 01/26468 | 4/2001 |
| WO | 2009/049747 A2 | 4/2009 |
| WO | 2009/091557 A1 | 7/2009 |
| WO | 2009/124707 A2 | 10/2009 |

OTHER PUBLICATIONS

International Search Report issued Oct. 23, 2014 in International Patent Appln. No. PCT/US14/58521 to FMC Corporation (10 pages).
International Search Report issued Oct. 21, 2014 in International Patent Application No. PCT/US14/58515 to FMC Corporation (11 pages).
International Search Report issued Oct. 23, 2014 in International Patent Application No. PCT/US14/58591 to FMC Corporation (11 pages).
International Search Report issued Nov. 5, 2014 in International Application No. PCT/US14/58569 to FMC Corporation (9 pages).
Merriam Webster Online dictionary, obtained online at: http://www.merriam-webster.com/dictionary/fertilizer, downloaded on Sep. 11, 2014.
International Search Report and Written Opinion mailed Jan. 4, 2016 in International Patent Application No. PCT/US2015/053104 (8 pages).
Database WPI, Week 201126, XP0002752081, Thomson Scientific, Dec. 15, 2010.
Database WPI, Week 201082, XP-002752082, Thomson Scientific, Oct. 6, 2010.
Kloepper, Joseph W. et al., Induced Systemic Resistance and Promotion of Plant Growth by *Bacillus* spp., Pytopathology, vol. 94, No. 11, 2004, 1259-1266.
International Search Report and Written Opinion mailed Feb. 13, 2015 in International Patent Application No. PCT/US2014/068571.
Ashland Safety Data Sheet for DEXTROL™ OC-180 dated May 21, 2015 (13 pages).
Safety Data Sheet for REXA® 88B dated Feb. 10, 2015 (15 pages).
Safety Data Sheet for "SOKOLAN CP9" dated Apr. 29, 2015 (9 pages).
Product label for AMMO 2.5 EC Insecticide (Cypermethrin)dated Jul. 31, 2012 (5 pages).
Safety Data Sheet for Attaflow® FL (Attapulgite Clay) dated Aug. 7, 2014 (10 pages).

(Continued)

*Primary Examiner* — Abigail Fisher
(74) *Attorney, Agent, or Firm* — FMC Corporation

(57) ABSTRACT

Methods of improving the growth of a plant by applying a plant growth effective amount of a plant growth composition that includes a hydrated aluminum-magnesium silicate and at least one dispersant selected from the group consisting of a sucrose ester, a lignosulfonate, an alkylpolyglycoside, a naphthalenesulfonic acid formaldehyde condensate and a phosphate ester to plant propagation material in the absence of insect pest pressure.

10 Claims, No Drawings

(56) References Cited

OTHER PUBLICATIONS

Product label for BRIGADE® 2EC Insecticide/Miticide (Bifenthrin) dated Oct. 2, 2012 (25 pages).
Product label for GLADIATOR™ insecticide/miticide (Zeta-Cypermethrin/Avermectin) dated Jul. 9, 2012 (23 pages).
Material Safety Data Sheet for Myconate HB (Formononetin) dated Sep. 8, 2009 (4 pages).
Product label for NUFOS® 4E insecticide (Chlorpyrifos) dated Dec. 20, 2012 (39 pages).
Extended label for RATCHET™ liquid dated Aug. 2011 (2 pages).
Safety Data Sheet for SOKALAN® CP 10 dated Mar. 9, 2015 (9 pages).
Product Label for TALSTAR PL GRANULAR insecticide dated Mar. 21, 2011 (3 pages).
Product Label for ZORO® Miticide/Insecticide (Abamectin) dated Mar. 29, 2012 (31 pages).
Third Party Observation submitted Mar. 30, 2016 relating to International Application No. PCT/US2014/068571 (5 pages).
Product Label for CAPTURE® LFR™ insecticide (Bifenthrin) dated Apr. 4, 2013 (19 pages).

* cited by examiner

METHODS FOR IMPROVING PLANT GROWTH

CROSS-REFERENCE TO RELATED APPLICATIONS

This application is a continuation of U.S. application Ser. No. 14/217,603, filed Mar. 18, 2014, which application claims the benefit under 35 U.S.C. §119(e) of U.S. Provisional Application Ser. No. 61/887,109, filed Oct. 4, 2013, the disclosure of which are incorporated herein by reference in their entirety.

FIELD OF THE INVENTION

The present invention is directed to methods of improving the growth of a plant by applying a plant growth effective amount of a plant growth composition that includes a hydrated aluminum-magnesium silicate and at least one dispersant selected from the group consisting of a sucrose ester, a lignosulfonate an alkylpolyglycoside, a naphthalenesulfonic acid formaldehyde condensate and a phosphate ester to plant propagation material in the absence of insect pest pressure.

BACKGROUND OF THE INVENTION

Due to the world's increasing population and decreasing amount of arable land, there is a pressing need for methods to increase the productivity of agricultural crops. Given this need to produce increased amounts of food and feed, plants are increasingly being grown in varied locations and/or under climactic conditions in which insect pressure does not exist. For example, more and more crops are being produced in greenhouses or other shelters where insect pressures can be easily minimized. Plants with increased cold and/or drought tolerance are being developed which may eventually permit them to grow under climactic conditions which are inhospitable to their traditional insect pests.

SUMMARY OF THE INVENTION

Some embodiments provide a method of improving the growth of a plant by applying a plant growth effective amount of a plant growth composition that includes a hydrated aluminum-magnesium silicate and at least one dispersant selected from a sucrose ester, a lignosulfonate, an alkylpolyglycoside, a naphthalenesulfonic acid formaldehyde condensate and a phosphate ester to plant propagation material in the absence of insect pest pressure.

In some embodiments, the plant growth composition includes: a) about 1% to about 20% of hydrated aluminum-magnesium silicate and b) about 0.2% to about 20% of at least one dispersant selected from a sucrose ester, a lignosulfonate, an alkylpolyglycoside, a naphthalenesulfonic acid formaldehyde condensate and a phosphate ester; where all % are % by weight based upon the total weight of all components in the composition.

In some embodiments, the plant propagation material is selected from seeds, spores, bulbs, cuttings, sets, rhizomes, tubers, meristem tissue, plant cells, and combinations thereof.

In some embodiments, the plant growth composition is applied at a rate ranging from 100 g/ha to 500g/ha. In other embodiments, the plant growth composition is applied at a rate ranging from 200 g/ha to 300 g/ha.

In some embodiments, the plant is selected from corn, cotton, soybean, sunflower, wheat, barley, rye, oat, and oilseed rape. In some embodiments, the plant growth composition further includes a liquid fertilizer. In other embodiments, the plant growth composition further includes at least one of an anti-freeze agent, an anti-foam agent and a biocide.

DETAILED DESCRIPTION OF THE INVENTION

The present invention is directed to methods of improving the growth of a plant by applying a plant growth effective amount of a plant growth composition that includes a hydrated aluminum-magnesium silicate and at least one dispersant selected from a sucrose ester, a lignosulfonate, an alkylpolyglycoside, a naphthalenesulfonic acid formaldehyde condensate and a phosphate ester to plant propagation material in the absence of insect pest pressure. Preferably, the plant growth composition includes a) about 1% to about 20% of hydrated aluminum-magnesium silicate and b) about 0.2% to about 20% of at least one dispersant selected from a sucrose ester, a lignosulfonate, an alkylpolyglycoside, a naphthalenesulfonic acid formaldehyde condensate and a phosphate ester; where all % are % by weight based upon the total weight of all components in the composition.

In another embodiment, the plant growth composition consists essentially of a hydrated aluminum-magnesium silicate and at least one dispersant selected from a sucrose ester, a lignosulfonate, an alkylpolyglycoside, a naphthalenesulfonic acid formaldehyde condensate and a phosphate ester. The composition according to this embodiment can include any additional components that do not materially affect the plant growth effectiveness of the previously-recited ingredients.

In a further embodiment, the plant growth composition consists of about 1% to 20% of a hydrated aluminum-magnesium silicate; about 0.2% to 20% of at least one dispersant selected from a sucrose ester, a lignosulfonate, an alkylpolyglycoside, a naphthalenesulfonic acid formaldehyde condensate and a phosphate ester; about 1% to 90% of an alkyl polyglycoside surfactant; about 0.001% to 1% of an antimicrobial preservative; about 0.001% to 1% of an anti-foam agent; about 1% to 20% of propylene glycol; and water.

The modifier "about" is used herein to indicate that certain preferred operating ranges, such as ranges for molar ratios for reactants, material amounts, and temperature, are not fixedly determined. The meaning will often be apparent to one of ordinary skill. For example, a recitation of a temperature range of about 120° C. to about 135° C. in reference to, for example, an organic chemical reaction would be interpreted to include other like temperatures that can be expected to favor a useful reaction rate for the reaction, such as 105° C. or 150° C. Where guidance from the experience of those of ordinary skill is lacking, guidance from the context is lacking, and where a more specific rule is not recited below, the "about" range shall be not more than 10% of the absolute value of an end point or 10% of the range recited, whichever is less.

As is employed herein, the term "plant growth effective amount" refers to an amount of a plant growth composition which will increase the growth and or vigor of the plant to an extent exceeding that of identical plants not treated with the plant growth composition. It is preferred that the rate of application of the plant growth composition be in the range of from about 100 grams of composition per hectare (g/ha) to about 500 g/ha, more preferably in a range of from about 200 g/ha to about 300 g/ha.

As is employed herein the term "plant propagation material" includes plant seeds, spores, bulbs, cuttings (e.g. stems, roots, leaves, and the like), sets, rhizomes, tubers, meristem tissue, single and multiple plant cells, and any other plant tissue from which a complete plant can be obtained.

The term "in the absence of insect pest pressure" includes situations in which insect pests are not present in the growth area of a plant, as well as situations where such insect pests are present within the area of growth of a plant but in a quantity which is not harmful to the plant and which does not interfere with the growth of the plant.

The improved plant growth obtained employing the methods of this invention include increased root length, increased shoot length and increased seedling weight, relative to plants which have not been so treated.

As is employed herein, the term "plants" includes agricultural, silvicultural and horticultural (including ornamental) plants. The term "plants" also includes genetically modified plants in which genetic material has been modified by the use of recombinant DNA techniques. Such techniques permit modifications that cannot readily be obtained by natural breeding or mutagenesis, such as, for example, cross-breeding under natural circumstances, natural mutations or natural recombination.

Preferred plants which may be treated in the process of this invention include, but are not limited to, barley; brassicas, such as broccoli, Chinese broccoli, Brussels sprouts, cauliflower, Cavalo broccoli, kohlrabi, cabbage, Chinese cabbage and Chinese mustard cabbage; cilantro; coriander; corn, cucurbits, such as chayote, Chinese waxgourd, citron melon, cucumber, gherkin, gourd, muskmelons (including cantalope, casaba, crenshaw melon, golden pershaw melon, honeydew melon, honey balls, mango melon, Persian melon, pineapple melon, Santa Claus melon and snake melon), pumpkins, summer squash, winter squash and watermelon; cotton plants; dried beans and peas, including bean, field bean, kidney bean, lima bean, pinto bean, navy bean, tepary bean, adzuki bean, fava bean, blackeyed pea, catjang, cowpea, crowder pea, moth bean, mung bean, rice bean, southern pea, urd bean, broad bean, chickpea, guar, lablab bean, lentil, pea, field pea and pigeon pea; eggplant; lettuce; leafy brassicas/turnip greens including broccoli raab, bok Choy, collards, kale, mizuna, mustard spinach, rape greens and turnip greens; oats; oilseed rape; okra; peppers; rapeseed; rye; sod; soybeans; spinach; succulent peas and beans including pea, dwarf pea, edible-pod pea, English pea, garden pea, green pea, snow pea, sugar snap pea, pigeon pea, bean, broadbean, fava bean, lima bean, runner bean, snap bean, wax bean, asparagus bean, yardlong bean, jackbean and sword bean; sunflowers; tobacco; tomatoes; tuberous and corm vegetables including potato, sweet potato, arracacha, arrowroot, Chinese artichoke, Jerusalem artichoke, edible canna, cassava, chayote, chufa, dasheen, ginger, leren, tanier, termer, yam bean and true yam; and wheat.

The plant growth composition may be applied to the propagative material by any means, including direct application, as a seed treatment, in furrow or band applications, by means well known to those in the art.

Optionally, the methods according to the present invention include applying a plant growth composition in combination with a liquid fertilizer.

The plant growth compositions used in the methods disclosed herein include a hydrated aluminum-magnesium silicate and at least one dispersant selected from the group consisting of a sucrose ester, a lignosulfonate, an alkylpolyglycoside, a naphthalenesulfonic acid formaldehyde condensate and a phosphate ester. The dispersant or dispersants are preferably present in a total concentration of from 0.02% by weight to 20% by weight based upon the total weight of all components in the composition.

In another embodiment, the plant growth composition includes a hydrated aluminum-magnesium silicate; at least one dispersant selected from the group consisting of a sucrose ester, a lignosulfonate, an alkylpolyglycoside, a naphthalenesulfonic acid formaldehyde condensate and a phosphate ester; and a liquid fertilizer. The term "liquid fertilizer" refers to a fertilizer in a fluid or liquid form containing various ratios of nitrogen, phosphorous and potassium (for example, but not limited to, 10% nitrogen, 34% phosphorous and 0% potassium) and micronutrients, commonly known as starter fertilizers that are high in phosphorus and promote rapid and vigorous root growth. The liquid fertilizer is preferably present in a concentration of from 95.00% by weight to 99.99% by weight based upon the total weight of all components in the formulation.

Optionally, the plant growth composition further includes at least one of an anti-freeze agent, an anti-foam agent and a biocide. These formulation components are well-known in the agrochemical arts. In one embodiment, the anti-freeze agent is a polyalkylene glycol, preferably propylene glycol, and when present, is present in an amount from about 1% to about 20% by weight, preferably from about 4% to about 10% of the total of all components in the composition. In an embodiment, the anti-foam agent is an alkylcyclotetrasiloxane, preferably an octamethylcyclo-tetrasiloxane silicone emulsion, for example, DOW CORNING® AF Emulsion or DOWCORNING® ANTIFOAM C Emulsion (Dow Corning Corporation). When present, the anti-foam agent is present in an amount of from about 0.001% to about 1% by weight, preferably from about 0.01% to about 0.5% of all the components in the total formulation. The preservative can be an isothiazolone or a mixture of isothiazolones, for example, KATHON® CG/ICP preservative or LEGEND® MK preservative (Rohm and Haas Corporation) or PROXEL™ BR preservative (Avecia Corporation). When present, the preservative is present in an amount of from about 0.001% to about 1% by weight, preferably from about 0.01% to about 0.5% of the total of all components in the formulation.

The hydrated aluminum-magnesium silicate is preferably selected from the group consisting of montmorillonite and attapulgite. The phosphate ester dispersant is preferably selected from the group consisting of a nonyl phenol phosphate ester and a tridecyl alcohol ethoxylated phosphate potassium salt.

The examples serve only to illustrate the invention and should not be interpreted as limiting since further modifications of the disclosed invention will be apparent to those skilled in the art. All such modifications are deemed to be within the scope of the invention as defined in the claims.

EXAMPLES

Preparation of Compositions

Plant Growth Composition A

A plant growth composition was prepared by combining 64.25 grams of water, 9.50 grams of propylene glycol, 7.00 grams of tridecyl alcohol ethoxylated phosphate potassium salt (Dextrol® OC-180 available from Dexter Chemical Corp), 8.00 grams of an alkyl d-glucopyranoside (Agnique®

9116 available from Cognis Corporation), 0.15 gram of polydimethylsiloxane (CowCorning® AF available from Dow Corning Corporation), 0.1 gram of an isothiazodone compound(Kathon® CG/ICP available from Rohm and Haas/Dow Chemicals) and 11.0 grams of attapulgite clay (Attaflow® FL available from Englehard). The mixture was stirred until homogenous.

Seed Treatment

Hybrid sweet corn seed (Incredible SE Yellow) was treated with either Plant Growth Composition A or a commercially available bifenthrin formulation (Capture® LFR). Corn seed (97.16 grams) was coated with 2.84 grams of Composition A in a seed coating apparatus and allowed to dry. Similarly, 97.12 grams of corn seed was coated with 2.84 grams of Capture® LFR and allowed to dry approximately 48 h prior to seeds being planted into a moist 50/50 Pennington soil/sand mixture. Seeds were inserted into a hole at a depth of 1". Twenty, 6" pots were set-up for each treatment with two corn seeds per pot (Total 40 seeds/Treatment). Pots were held under greenhouse conditions for 17 days on an Ebb and Flow bench to allow for equal irrigation between treatments and replicates. Corn heights were measured at 5, 7, 10, 12, 14, and 17 days after planting (DAP). At 17 DAP, each plant was extracted from the soil and evaluated for shoot length, root length, wet shoot weight, and wet root weight. Roots and shoots were placed within a drying oven at approximately 60° C. At 4 and 7 days after plant extraction, dry shoot and root weights were evaluated. An untreated check was also evaluated.

Results

Composition A and Capture® LFR treatments provided greatly improved root growth, shoot growth, root weight, and shoot weight when compared to the untreated seed. The average percent seed germination per treatment is presented in Table 1.

TABLE 1

Average percent germination by corn seed treatment and evaluation interval

| | 5 DAP | 7 DAP | 10 DAP | 12 DAP | 14 DAP | 17 DAP |
|---|---|---|---|---|---|---|
| Composition A | 55.0 | 67.5 | 67.5 | 67.5 | 67.5 | 67.5 |
| Capture ®LFR | 55.0 | 70.0 | 75.0 | 75.0 | 75.0 | 75.0 |
| Untreated Check | 42.5 | 60.0 | 62.5 | 65.0 | 62.5 | 62.5 |

The wet weights of each shoot and root were measured at 17 DAP (Table 2 & 3) and correlated well to dry weights after 7 days of drying; dry weights were assessed at 4 and 7 days after inserted into a drying oven at 60° C.

TABLE 2

Average weight reduction of corn shoots and roots weighed immediately after soil extraction (wet) compared to 4 and 7 days within the drying oven (dry)

| | Shoot Weight (gams) | | Root Weight (grams) | | |
|---|---|---|---|---|---|
| Treatment | Wet | Dry (4d) | Wet | Dry (4d) | Dry (7d) |
| Composition A | 1.86 | 0.16 | 1.57 | 0.25 | 0.25 |
| Cpature ® LFR | 1.72 | 0.15 | 1.64 | 0.3 | 0.29 |
| Untreated Control | 1.37 | 0.12 | 1.16 | 0.21 | 0.19 |

The corn shoot height was measured at 5, 7, 10, 12, 14 and 17 days after planting and the root length was measured after removing each plant from the soil and cleaning the roots with water. The average of these measurements is summarized in Table 3 below.

TABLE 3

Average shoot height (cm) and root length (cm) at varying evaluation dates

| | Shoot Height | | | | | | Root Length |
|---|---|---|---|---|---|---|---|
| Treatment | 5 DAP | 7 DAP | 10 DAP | 12 DAP | 14 DAP | 17 DAP | 17 DAP |
| Composition A | 2.5 | 4.5 | 13.3 | 20.0 | 25.0 | 32.0 | 20.37 |
| Capture ® LFR | 2.4 | 4.4 | 12.4 | 19.0 | 24.0 | 30.0 | 19.41 |
| Untreated Control | 2.0 | 3.2 | 10.10 | 14.0 | 20.0 | 28.0 | 15.09 |

While this invention has been described with an emphasis upon preferred embodiments, it will be obvious to those of ordinary skill in the art that variations in the preferred compositions and methods may be used and that it is intended that the invention may be practiced otherwise than as specifically described herein. Accordingly, this invention includes all modifications encompassed within the spirit and scope of the invention as defined by the claims that follow.

What is claimed is:

1. A plant composition obtained after treatment of plant propagation material, the treatment comprising the step of applying a plant growth effective amount of a plant growth composition to the plant propagation material, said plant growth composition comprising:
   a) a hydrated aluminum-magnesium silicate; and
   b) at least one dispersant selected from the group consisting of a sucrose ester, a lignosulfonate, an alkylpolyglycoside, a naphthalenesulfonic acid formaldehyde condensate and a phosphate ester;
wherein the plant growth composition is free of biocides.

2. The plant composition of claim 1, wherein the plant growth composition comprises: about 0.2% to about 20% of at least one dispersant selected from the group consisting of a sucrose ester, a lignosulfonate, an alkylpolyglycoside, a naphthalenesulfonic acid formaldehyde condensate and a phosphate ester; wherein all % are % by weight based on the total weight of all components in the composition.

3. The plant composition of claim 1, wherein the plant propagation material is selected from the group consisting of seeds, spores, bulbs, cuttings, sets, rhizomes, tubers, meristem tissue, plant cells, and combinations of two or more thereof.

4. The plant composition of claim 3, wherein the plant propagation material comprises at least one seed.

5. The plant composition of claim 1, wherein the plant growth composition is applied at a rate ranging from 100 g/ha to 500 g/ha.

6. The plant composition of claim 5, wherein the plant growth composition is applied at a rate ranging from 200 g/ha to 300 g/ha.

7. The plant composition of claim 1, wherein the plant is selected from the group consisting of corn, cotton, soybean, sunflower, wheat, barley, rye, oat, and oilseed rape.

8. The plant composition of claim 1, wherein the plant growth composition further comprises a liquid fertilizer.

9. The plant composition of claim 1, further comprising an alkylpolyglycoside surfactant in about 1% to about 90%, an antifoam agent in about 0.001% to about 1%, and an antifreeze agent in about 1% to about 20%, wherein all % are % by weight based on the total weight of all components in the composition.

10. A composition suitable for use in improving the growth of a plant, the composition consisting:

a) a hydrated aluminum-magnesium silicate;

b) at least one dispersant selected from the group consisting of a sucrose ester, a lignosulfonate, an alkylpolyglycoside, a naphthalenesulfonic acid formaldehyde condensate and a phosphate ester;

c) an alkylpolyglycoside surfactant;

d) a preservative;

e) an antifoam agent;

f) an antifreeze agent; and g) water.

* * * * *